(12) United States Patent
Chakrabortty et al.

(10) Patent No.: US 8,545,901 B2
(45) Date of Patent: Oct. 1, 2013

(54) **TOPICAL COMPOSITION COMPRISING EXTRACTS OF *A. INDICA* AND *M. CHARANTIA* OR *S. INDICUM***

(75) Inventors: Amit Chakrabortty, Bangalore (IN); Rajendra Mohan Dobriyal, Bangalore (IN); Vidula Iyer, Bangalore (IN); Nirmala Nair, Bangalore (IN); Shilpa Atul Vora, Bangalore (IN)

(73) Assignee: Conopco Inc., Englewood Cliffs, NJ (US)

(*) Notice: Subject to any disclaimer, the term of this patent is extended or adjusted under 35 U.S.C. 154(b) by 119 days.

(21) Appl. No.: 13/124,668

(22) PCT Filed: Oct. 16, 2009

(86) PCT No.: PCT/EP2009/063571
§ 371 (c)(1),
(2), (4) Date: Jun. 1, 2011

(87) PCT Pub. No.: WO2010/046316
PCT Pub. Date: Apr. 29, 2010

(65) Prior Publication Data
US 2011/0236509 A1 Sep. 29, 2011

(30) Foreign Application Priority Data
Oct. 24, 2008 (IN) .......................... 2296/MUM/2008

(51) Int. Cl.
*A61K 36/00* (2006.01)
*A61K 36/58* (2006.01)

(52) U.S. Cl.
USPC .......................................... 424/725; 424/761

(58) Field of Classification Search
None
See application file for complete search history.

(56) References Cited

U.S. PATENT DOCUMENTS

| | | | |
|---|---|---|---|
| 6,294,571 B1 * | 9/2001 | Subbaraman et al. | 514/453 |
| 6,811,790 B1 * | 11/2004 | Damaria et al. | 424/406 |
| 2007/0014749 A1 * | 1/2007 | Shah | 424/74 |
| 2008/0045594 A1 | 2/2008 | Piccirilli | |

FOREIGN PATENT DOCUMENTS

| | | |
|---|---|---|
| DE | 19528575 A1 | 2/1997 |
| GB | 2353706 | 3/2001 |
| JP | 10279428 | 10/1998 |
| JP | 2002212050 | 7/2002 |
| KR | 2003017295 | 3/2003 |
| KR | 2003017295 A | 3/2003 |
| WO | WO0105417 A1 | 1/2001 |
| WO | WO2006021660 A1 | 3/2006 |

OTHER PUBLICATIONS

Jain et al.,Inhibition of Propionibacterium acnes-induced mediators of inflammation by Indian herbs, Phytomedicine,Jan. 1, 2003,34-38,10,Urban and Fischer Verlag.
Ajose,Some Nigerian plants of dermatologic importance,International Journal of Dermatology ,Jan. 1, 2007,48-55,vol. 46, Suppl. 1.
Ramakrishnan et al.,Antihyperglycaemic effect of Diamed, a herbal formulation, in experimental diabetes in rats, Journal of Pharmacy and Pharmacology,Jan. 1, 2001,1139-1143,vol. 53 No. 8.
Muhaasa,Key Attributes of TKDL,SCIR—Abstract,Apr. 29, 2000,421-422.
Schonfelder et al.,*Sesamum indicum* L. (*S. orientale* L.),Indischer Sesam,Jan. 1, 2004,412-413.
International Search Report PCT/EP2009/063571 dated Jun. 7, 2010.
European Search Report in EP application EP 09 15 3931 dated Jan. 11, 2010.

* cited by examiner

*Primary Examiner* — Qiuwen Mi
(74) *Attorney, Agent, or Firm* — Karen E. Klumas

(57) ABSTRACT

The invention relates to a topical composition and a method for reducing or preventing occurrence of acne on the skin. It is an object of the present invention to provide for a combination of herbal extracts that interact synergistically to provide a cosmetic composition for prevention, reduction or treatment of acne. The present invention provides for a topical composition comprising (i) an extract of a first active which is *Azhadirachta indica*; and (ii) an extract of a second active selected from *Momordica charantia* or *Sesamum indicum*.

6 Claims, No Drawings

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: from prior art
<220> FEATURE:
<221> NAME/KEY: primer
<222> LOCATION: (1)..(21)

<400> SEQUENCE: 1
gtgggccgct ctaggcacca a        21

<210> SEQ ID NO 2
<211> LENGTH: 23
<212> TYPE: DNA
<213> ORGANISM: Artificial Sequence
<220> FEATURE:
<223> OTHER INFORMATION: from prior art
<220> FEATURE:
<221> NAME/KEY: primer
<222> LOCATION: (1)..(23)

<400> SEQUENCE: 2
ccaaagtaga cctgcccgga ctc        23

<210> SEQ ID NO 3
<211> LENGTH: 20
<212> TYPE: DNA
<213> ORGANISM: Artificial Sequence
<220> FEATURE:
<223> OTHER INFORMATION: from prior art
<220> FEATURE:
<221> NAME/KEY: Primer
<222> LOCATION: (1)..(20)

<400> SEQUENCE: 3
ctcctcaaga ctgttcctcc        20

<210> SEQ ID NO 4
<211> LENGTH: 24
<212> TYPE: DNA
<213> ORGANISM: Artificial Sequence
<220> FEATURE:
<223> OTHER INFORMATION: from prior art
<220> FEATURE:
<221> NAME/KEY: primer
<222> LOCATION: (1)..(24)

<400> SEQUENCE: 4
gcagtcatgt gcttttcctc ttgc        24

TOPICAL COMPOSITION COMPRISING EXTRACTS OF *A. INDICA* AND *M. CHARANTIA* OR *S. INDICUM*

The invention relates to a topical composition and a method for reducing or preventing occurrence of acne on the skin.

Acne, also known as Acne vulgaris, is a common skin condition that affects nearly all adolescents and adults at some times in their lives. It has a complex etiology, involving abnormal keratinization, excess sebum production, androgen function, bacterial growth, and immune hypersensitivity. Although one or more of the above processes is correlated with acne, the one triggering factor and the exact sequence of events leading to the formation of acne lesions is not been fully understood. Other factors which have been linked to acne are presence of free radicals with subsequent oxidative stress leading to cellular damage. It has been observed that acne usually occurs in areas rich in sebaceous glands like the face, neck and back. A bacteria *Propionibacterium acnes* (*P. acnes*) has also been implicated in occurrence of acne.

The earliest acne lesion is known as the microcomedone. These evolve into comedones which may either be open ("blackhead") or closed ("whitehead"). The various stages of acne have been classified as comedones, papules, pustules, and cysts.

Acne has been treated in many ways. Most treatments take several weeks to months before a noticeable change is seen. Benzoyl peroxide which has an antibacterial effect has been used for mild cases of comedones and is also believed to prevent formation of other comedones. Tretinoin which is a derivative of Vitamin A has been used in the treatment of whiteheads and blackheads and is believed to convert closed comedones into open comedones. Isotretinoin has been used to treat severe cystic acne. Azelaic acid has been used to treat acne and is believed to act by inhibiting growth of *P. Acnes* and by decreasing the ductal hypercornification. In very severe cases of acne, antibiotics like tetracycline, erythromycin and clindamycin have been used. Antibiotics are believed to work by several mechanisms, the most important being the decrease in the number of bacteria in and around the follicle. They are also thought to reduce the irritating chemicals produced by the white blood cells in the sebum, thereby reducing the inflammatory response.

Most of the treatments, involve use of synthetic chemicals. Many people do not prefer use of synthetic chemicals since they are believed to be harsh on the human body. Some people believe that synthetic chemicals cause side effects. Hence, more and more people prefer use of materials which are "natural" e.g. actives based on herbal origin. Jain, A. and Basal, E. in the article "Inhibition of *Propionibacterium acnes*—induced mediators of inflammation by Indian herb", in the Journal *Phytomedicine*, 2003, 10:34-38 have indicated that herbs like *Rubia Cordifolia*, *Curcuma longa*, *Hemidesmus indicus* and *Azadirachta indica* have the capacity to suppress *P. Acnes* induced inflammatory mediators.

The present inventors have also been working towards providing such "natural" solutions to solving the problem of acne. They tried a large number of combinations of herbal extracts and found that two specific combinations of herbs interact synergistically to help solve the problem of acne.

Use of some of these herbs for skin benefit are described below.

WO2001005417 claims a process for treating skin having acne or furuncle comprising applying a composition containing an extract of *Momordica charantia* L. over an area of skin having acne or furuncle.

JP2002212050 claims a cosmetic exhibiting beauty promoting effects, promoting metabolism of the skin without damaging the skin, smoothing the skin and also providing prevention of acne, skin chapping and skin aging when directly applied to the skin as an external preparation. The cosmetic is prepared by formulating an extract or a squeezed liquid from fruit of balsam pear (family Cucurbitaceae; scientific name is *Momordica charantia*) to a base of the cosmetic for the skin or the hair.

US20070014749 relates to the preparation and use of compositions for the treatment of skin disorders itchy and/or infected skin such as impetigo, acne (on face, forehead scalp and on the back of the body) and fungal infection of skin and nails. The skin composition comprises freeze dried water extracts of *Cassia tora*, *Melia azadirachta*, and *Centratherum anthelminticum*.

JP10279428A claims a stable, highly safe, cosmetic having skin whitening effect by including (A) 0.01-20.0 wt. % of a water-soluble extract from Sesamum Indicum L. and (B) as necessary, an aqueous ingredient, powder, surfactant, lubricant, moisturizer, alcohol(s), pH adjustor, antiseptic, color, antioxidant, ultraviolet light absorber, thickening agent, perfume, skin-beautifying ingredient, etc. The ingredient A is obtained by removing, as necessary, lipid components from the roots, leaves, stems, buds, flowers, germinated matter or seeds of *Sesamum Indicum* L. or dried product(s) and/or ground product(s) thereof by use of a water-insoluble organic solvent followed by conducting an extraction with water or a hydrous and/or anhydrous lower alcohol.

Thus, although each of the herbs have been used in skin preparation, none of the above cited prior art disclose or suggest a synergistic combination of the herb extracts found by the present inventors to give benefits in acne treatment.

It is thus an object of the present invention to provide for a combination of herbal extracts that interact synergistically to provide a cosmetic composition for prevention, reduction or treatment of acne.

The present invention provides for a topical composition comprising
(i) an extract of a first active which is *Azhadirachta indica*; and
(ii) an extract of a second active selected from *Momordica charantia* or *Sesamum indicum*.

In a further embodiment, there is provided a composition comprising
(i) an extract of a first active which is *Azhadirachta indica*; and
(ii) an extract of a second active selected from *Momordica charantia* or *Sesamum indicum*
for use in preventing, reducing or treating acne.

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated.

Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

The present invention provides for a topical composition comprising a mixture of extracts of two herbal actives. The first active is the herb *Azhadirachta indica*. The second active is a herb selected from either *Momordica charantia* or *Sesamum indicum*. It is particularly preferred that the extract is a water extract.

*Azadirachta indica*, also known as *Melia azadirachta*, is a large evergreen tree which can grow up to a height of 18 meters and can have a girth of up to 2.4 meters. It grows in the wild throughout India and in similar tropical climatic countries. It is also cultivated widely in India. The tree is deeply associated with Indian culture and is known as Neem, Nim, Nimba, Nimb, Veppa, Bevinamara, Limba, Vembu etc. in different languages of India. Outside India, the tree is known as Indian Lilac, Margosa or Neem Tree. The extract of neem for use in the present invention is preferably from the leaves of the neem tree. Leaves of neem have been used in the traditional Indian medicinal system known as Ayurveda for treatment of various disorders. It has been reported to be used in treating various skin disorders, and for preventing wound infections. Decoction of the leaves is added to bath water to get rid of skin problems. Poultice of the leaves is also used in inflammation associated with wounds. The leaves are also used as an insect repellent. Neem leaves are used internally as an anthelmintic agent.

Neem leaves are reported to contain various physiologically active compounds like stigmasterol, nimbocinone, nimbocinolide, isonimbocinolide, nimocinol, isonimocinolide and isoazadirolide. The fresh green leaves yield compounds like meldenindiol, vilasinin, azadirachtanin, margosinolide, isomargosinolide, and desacetyldihydronimbic acid.

Extract of the first active, i.e. extract of *Azadirachta indica*, is preferably present in 0.01 to 2% by weight of the composition, conveniently 0.1 to 1% by weight of the composition.

The second active is a herb selected from *Momordica charantia* or *Sesamum indicum*.

*Momordica charantia*, commonly known as karela in India, is a cucurbitaceous climber cultivated throughout the tropical climate across the globe. The herb is also called bitter melon, bitter gourd, balsampear, kaippavalli, pavakka in different languages. The unripe fruit is a popular bitter vegetable. It is also used in traditional Indian medicine, mostly for the management of diabetes.

Ayurveda, the traditional Indian form of medicine, uses karela fruit as laxative, anti-pyretic and as an appetizer. It is used in Ayurveda to improve liver functions and to purify the blood. Fruits are eaten as food and used in treatment of arthritis, gout, liver and spleen enlargement.

A number of novel and biologically active phytochemicals have been identified from karela fruits including charantin, momordicin, momordin, momordicosides, and polypeptides. However, those which are attributed with therapeutic activity include polypeptide-p, charantin and Momordin. Some other compound like vicine has also been reported to posses some hypoglycemic activity.

As per the present invention, the fruit of the karela plant is preferably used for preparing the extract.

*Sesamum indicum* is also known as *Sesamum orientate*. The common name is sesame. It is an erect, branched plant that grows to a height of about 60-180 cm. It is an annual plant. It is cultivated throughout the plains of India and also in the hills up to an altitude of about 1200 meters. It is also grown in other countries having climatic conditions like the tropical plains of India mostly as a source of oil seed. It is also used as a spice for seasonings. Sesame is known as Tila, Till, Til, or Gingelli in different regions of India. There are many varieties of sesame grown in India. The varieties are based on the colour of the seed coat which ranges from white to black. There are many intermediate varieties as well. However, the black and white Sesame are two varities largely cultivated in India.

Of these two varities, the white sesame is more preferred for use in the present invention.

The extract of the second active is preferably present in 0.01 to 2% by weight of the composition, conveniently 0.1 to 1.0% by weight of the composition.

The composition of the invention preferably comprises a cosmetically acceptable vehicle. The cosmetically acceptable vehicle is suitably chosen to provide the skin care composition in any one of the well known cosmetic formats. Such formats may be leave-on topical compositions or wash-off products. Well known leave-on formats include cream, gel, lotion, ointment, powder, mousse or spray. More preferred formats are the oil-in-water emulsions like cream or lotion, most preferred being cream. Among the creams, the vanishing cream base is most preferred. By a vanishing cream base is meant a base which has 5 to 25% $C_{12}$-$C_{20}$ fatty acids and 0.1-10% fatty acid soap by weight of the topical composition. Vanishing cream base gives a highly appreciated matty feel to the skin. Although $C_{12}$ to $C_{20}$ fatty acids are especially preferred for the present invention, more preferred are $C_{14}$ to $C_{18}$ fatty acids. The most preferred fatty acid is stearic acid. The fatty acid is more preferably present in 5 to 20% by weight of the composition. Soaps in the vanishing cream base include alkali metal salt of fatty acids, like sodium or potassium salts, most preferred being potassium stearate. The soap in the vanishing cream base is generally present in an amount in the range of 0.1 to 10%, more preferably 0.1 to 3% by weight of the composition. Generally, the vanishing cream base in cosmetic compositions is prepared by taking a desired amount of total fatty matter and mixing with potassium hydroxide in desired amounts. The soap is usually formed in situ during the mixing.

The other preferred cosmetically acceptable vehicle is a detergent composition. The detergent composition preferably comprises 5 to 85% salt of fatty acid or 2 to 20% synthetic surfactant or mixtures thereof.

The topical composition may comprise an optional ingredient like a skin lightening agent. The skin lightening agent is preferably chosen from one or more of a vitamin B3 compound or its derivative e.g. niacin, nicotinic acid, niacinamide or other well known skin lightening agents e.g. aloe extract, ammonium lactate, arbutin, azelaic acid, kojic acid, butyl hydroxy toluene, citrate esters, 2,5 dihydroxybenzoic acid and its derivatives, ellagic acid, fennel extract, gluconic acid, glycolic acid, green tea extract, hydroquinone, 4 hydroxyanisole and its derivatives, 4-hydroxy benzoic acid derivatives, kojic acid, lactic acid, lemon extract, linoleic acid, magnesium ascorbyl phosphate, 2,4 resorcinol derivatives, 3,5 resorcinol derivatives, salicylic acid, and vitamins like vitamin B6, vitamin B12, vitamin C, vitamin A, a dicarboxylic acid, extracts from plants viz. rubia and symplocos, hydroxycarboxylic acid like lactic acid and their salts e.g. sodium lactate, and mixtures thereof. The preferred skin lightening agent for use in the composition of the invention is a vitamin B3 compound. Skin lightening agent, when used, is preferably present in an amount in the range of 0.1 to 10%, more preferably 0.2 to 5% by weight of the composition.

Another optional ingredient in the topical composition is a UV sunscreen. The UV sunscreen may be inorganic or organic. Suitable organic sunscreen agents include 2-hydroxy-4-methoxybenzophenone, octyldimethyl-p-aminobenzoic acid, 2,2-dihydroxy-4-methoxybenzophenone, 2-ethylhexyl-2-cyano-3,3-diphenylacrylate, 2-ethylhexylsalicylate, 2-ethylhexyl-p-dimethyl-amino-benzoate, 2-ethylhexyl-p-methoxycinnamate, butylmethoxydibenzoylmethane, 2-hydroxy-4-methoxybenzophenone, octyldimethyl-p-aminobenzoic acid and mixtures thereof. Most suitable organic sunscreen are 2-ethylhexyl-p-methoxycinnamate or butylmethoxydibenzoylmethane. The composition preferably comprises from about 0.1% to about 10%, more preferably from about 0.1% to about 5%, sunscreen agent by weight of the composition.

Inorganic UV sunscreens can be called sunblocks. Preferred sunblocks include zinc oxide, iron oxide, silica, such as fumed silica, and titanium dioxide. Most suitable sunblocks are zinc oxide or titanium dioxide. The sun block is preferably incorporated in 0.1 to 5% by weight of the composition.

The composition according to the invention may also comprise other diluents. The diluents act as a dispersant or carrier for other materials present in the composition, so as to facilitate their distribution when the composition is applied to the skin.

Diluents other than water can include liquid or solid emollients, solvents, humectants, thickeners and powders.

The cosmetically acceptable vehicle is preferably present from 10 to 99.9%, preferably from 50 to 99% by weight of the composition, and can, in the absence of other cosmetic adjuncts, form the balance of the composition.

The compositions of the present invention can comprise a wide range of other optional ingredients. Examples of such optional ingredients include antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

According to another aspect of the present invention there is provided a method of preventing or reducing the occurrence of or treating acne comprising the step of applying to the skin a composition of the present invention.

According to yet another aspect of the present invention there is provided use of a composition comprising an extract of a first active which is *Azhadirachta indica*; and an extract of a second active selected from *Momordica charantia* or *Sesamum indicum* for preventing or reducing the occurrence of or treating acne. The use of the composition of the invention is preferably for non-therapeutic benefits.

The invention is now further described by way of the following non-limiting examples.

EXAMPLES

The efficacy of the extract of the actives for treating/prevention of acne was tested using an assay that measured the expression of involucrin mRNA. In acne there is an abnormality in proliferation and differentiation. Involucrin marker has been used for the screening studies. The procedure used was as follows:

Cell Culture

HaCaT human keratinocytes obtained from Dr Fusenig, Germany. The cells were cultured in Dulbecco's modified eagle's media (Sigma Chemical Co., USA) supplemented with 10 U/ml penicillin G, 0.1 mg/ml streptomycin sulfate, 10 mM HEPES buffer and 10% heat inactivated fetal calf serum (Gibco, USA) at 37° C. in a humidified incubator with 5% $CO_2$ atmosphere.

Reagents

All the chemical reagents were procured from Sigma Chemical Co., USA. Retinoic acid, 13-cis retinoic acid and testosterone stocks were prepared in dimethyl sulfoxide (DMSO).

Preparation of Extract of Actives 1 gm of each of the powdered actives was soaked in 60 ml of water overnight. The next day the sample was boiled until the volume was reduced to 10 ml (final concentration equivalent to 1 gm/10 ml) for a total for 4 hrs. This extract was filtered and cooled and used for the in vitro assays at a final concentration of 0.01%.

| Actives | stock solutions | final concentration in media |
| --- | --- | --- |
| Retinoic acid | $10^{-4}$M | $10^{-6}$M |
| 13-cis retinoic acid | $10^{-6}$M | $10^{-8}$M |
| Testosterone | $10^{-7}$M | $10^{-9}$M |
| DMSO | 100% | 0.01% |
| Extracts of actives | 1% | 0.01% |

RT-PCR $5 \times 10^5$ keratinocytes were plated in a 35 mm plate and incubated at 37° C. in 5% $CO_2$ for 24 hrs. Actives were added the next day and cells were harvested 18-24 hrs later. Total cellular RNA was then extracted from these cells using TR1 reagent (Sigma Chemical Co., USA) as recommended by the supplier. cDNA synthesis was carried out using oligo (dT)18 primer. Semi-quantitative RT-PCR was then carried out using specific, forward and reverse primers as listed below. The PCR was carried out in Perkin Elmer Gene Amp PCR system 2400 for 30 cycles in all cases. The PCR products were analysed on 1-2% agarose gels and detected by ethidium bromide staining. The DNA gel picture was captured and the intensities of the PCR amplified DNA fragments were analysed using PhotoCap image analysis software (Vilber Lourmat, France).

The following primers were used for PCR amplification:

| Primer | Sequence | Product size | Annealing temperature |
| --- | --- | --- | --- |
| Beta actin | | | |
| Forward | 5'-GTG GGC CGC TCT AGG CAC CAA-3' | 300 bp | 60° C. |
| Reverse | 5'-CCA AAG TAG ACC TGC CCG GAC TC-3' | | |
| Involucrin | | | |
| Forward | 5'-CTC CTC AAG ACT GTT CCT CC-3' | 143 bp | 64° C. |
| Reverse | 5'-GCA GTC ATG TGC TTT TCC TCT TGC-3' | | |

The involucrin expression as a percentage of control was calculated using the following procedure:

(Control−Active)×100/Control

The data on the various samples of Extracts of actives are summarized in Table 1. The total concentration of the active was 0.01% in the assay. The control sample was water.

TABLE 1

| Example | Active | Involucrin expression as a percentage of control |
|---------|--------|--------------------------------------------------|
| 1 | Control | 100 |
| 2 | *Azhadirachta indica* | 94.2 |
| 3 | *Momordica charantia* | 80.7 |
| 4 | *Sesamum indicum* | 119.3 |
| 5 | *Azhadirachta indica* + *Momordica charantia* | 49.1 |

TABLE 1-continued

| Example | Active | Involucrin expression as a percentage of control |
|---------|--------|--------------------------------------------------|
| 6 | *Azhadirachta indica* + *Sesamum indicum* | 24.5 |

The data in Table 1 indicates that a combination of an extract of a first active which is *Azhadirachta indica* and an extract of a second active selected from *Momordica charantia* or *Sesamum indicum* interact synergistically to provide a composition for prevention, reduction or treatment of acne.

The invention claimed is:

1. A composition comprising
   (i) 0.01 to 2% by weight of the composition of a water extract of a first active which is *Azadirachta indica*; and
   (ii) 0.01 to 2% by weight of the composition of a water extract of a second active selected from *Momordica charantia* or *Sesamum indicum*,
wherein the composition is the form of a topical composition for application to skin.

2. A composition as claimed claim 1 comprising a cosmetically acceptable vehicle.

3. A composition as claimed in claim 2 wherein the cosmetically acceptable vehicle is either a water-in-oil emulsion or a detergent composition.

4. A composition as claimed in claim 3 wherein the emulsion comprises (i) 5-25% by weight $C_{12}$-$C_{20}$ fatty acids and (ii) 0.1-10% by weight fatty acid soap by weight of the topical composition.

5. A composition as claimed in claim 3 wherein the detergent composition comprises 5 to 85% salt of fatty acid or 2 to 20% synthetic surfactant or mixture thereof.

6. A method of reducing the occurrence of or treating acne comprising the step of applying to the skin a composition as claimed in claim 1.

* * * * *